United States Patent [19]

Jeffras et al.

[11] 4,311,052
[45] Jan. 19, 1982

[54] ULTRASONIC CONTROL CONTOUR FOLLOWER

[75] Inventors: Nathaniel B. Jeffras; Donald R. Modispacher, both of Woodland Hills, Calif.

[73] Assignee: Automation Industries, Inc., Greenwich, Conn.

[21] Appl. No.: 2,732

[22] Filed: Jan. 11, 1979

[51] Int. Cl.³ ............................................. G01N 29/00
[52] U.S. Cl. .................................................. 73/634
[58] Field of Search ............... 73/618, 619, 620, 621, 73/624, 625, 632, 633, 634, 640

[56] References Cited

U.S. PATENT DOCUMENTS

| | | | |
|---|---|---|---|
| 3,575,043 | 4/1971 | Allen et al. | 73/619 |
| 3,898,838 | 8/1975 | Connelly | 73/634 |
| 3,969,926 | 7/1976 | Walker et al. | 73/620 |
| 4,140,954 | 2/1979 | Jeffras et al. | 73/619 |

Primary Examiner—Stephen A. Kreitman
Attorney, Agent, or Firm—Francis N. Carten

[57] ABSTRACT

The material tester has three mutually perpendicular directions of motion and a rotary motion about an upright axis. Ultrasonic search units are mounted for motion on or about these axes and are connected to control the speeds along several of the axes and about the vertical axis as well as to produce a signal showing the properties of the material to be tested. The search units are controlled by the motion along the several axes and about an upright axis to follow a contour.

32 Claims, 6 Drawing Figures

ULTRASONIC CONTROL CONTOUR FOLLOWER

BACKGROUND

Presently it is conventional to inspect a workpiece for flaws or defects contained therein by ultrasonic nondestructive testing methods. These methods employ an ultrasonic transducer such as a piezoelectric crystal which when energized by an electrical stimulus radiates a pulse of ultrasonic energy into a workpiece. If the familiar pulse echo search unit is used, the ultrasonic energy is reflected back from a defect within the workpiece to the crystal whereby the mechanical vibrations caused by the ultrasonic energy are translated back into electrical signals. In this method the time of arrival of the return signal indicates the presence and exact location of the defect within the workpiece. On the other hand, when the familiar "through" transmission system is used a separate transducer is aligned opposite the workpiece and attenuations due to the defects in the workpiece or changes in the time of arrival of the signal is indicative of some characteristics of the workpiece.

This invention is directed to a testing machine wherein an ultrasonic testing search unit is moved along a contoured surface of a structure being tested. The test instrument is provided with equipment to produce liquid coupling between the search units and the contour of the structure being followed and tested.

Certain workpieces include curved or sloped shapes which are sometimes difficult to maneuver a search unit across. A number of different type systems have been employed to ultrasonically test curved or sloped workpieces. One such device is described in U.S. Pat. No. 3,721,118 and copending application for United States Letters Patent, Ser. No. 766,688, filed Feb. 2, 1977, now U.S. Pat. No. 4,140,954, both assigned to Automation Industries, the assignee of this invention. Ultrasonic search units for such testing are coupled to the workpiece being tested by use of liquid couplants. The liquid is injected into the space between the face of the search unit and the contoured surface. In view of the liquid coupling, the search unit should be located very close to the contoured surface. As a result of this, testing with presently available equipment is slow because of these constraints. In order to make such testing economic, and, accordingly, widely used, it is necessary to create a machine and a control system which permits rapid and accurate testing.

In general, the principle on which ultrasonic testing is based is the projection of ultrasonic energy into the workpiece with consequent reflection or transmission depending upon the nature of the workpiece. Testing may be accomplished either by analyzing the reflected portion of the signal or by analyzing the portion that is transmitted through the workpiece. In reflection type of ultrasonic analysis, both the transmitter search unit and the receiver are on the same side of the workpiece. In the case of through transmission testing, the transmitter search unit is located on one side of the workpiece while the receiver is located on the other side.

Under such circumstances, it is also necessary to provide a machine which accurately positions the receiver search units in alignment with and facing the transmitter search unit, while the transmitter search unit follows the contour of the part being tested.

SUMMARY

The invention is directed to a testing machine wherein the machine is structured to move testing devices along the contour of a workpiece being tested, and particularly ultrasonic search units for testing the structure. The machine moves the search units on two horizontally perpendicular and two vertically parallel axes during normal testing and rotates the testing units on a vertical axis so that continuous contour following is achieved for proper positioning of the search units with respect to the device being tested.

It is thus an object of this invention to provide a contour following device whereby testing of the contour can be achieved. It is a further object to provide a machine wherein test units are moved along a contour for the testing of the contour. It is a further object to provide a testing machine wherein ultrasonic search units are liquid-coupled to the surface to be tested. It is another object to control the motion of the contour following of the machine so that the ultrasonic search units are properly positioned for optimum testing and for controlling the search velocity along the several axes to establish a substantially constant surface velocity of the testing.

It is a further object to provide an ultrasonically controlled contour following and testing machine wherein ultrasonic through testing can be achieved by positioning the search unit receiver directly opposite the search unit transmitter so that through transmission ultrasonic testing is achieved.

It is a further object to provide a testing machine wherein ultrasonic search units can be precisely positioned as they move over smooth, horizontal curved surfaces such as airfoil shape with the search units being positioned by the structure being tested rather than by following a preset path. It is another object to provide for the automatic testing of irregular cross-section such as are found in stepped or tapered parts. It is a further object to provide for the automatic testing of structures with compound curves, such as dish-shaped antennas.

Other objects and advantages of this invention will become apparent from the study of the following portion of the specification, the claims and the attached drawings.

These and other objects of the instant invention are accomplished generally speaking by providing an ultrasonic contour following and testing machine. A support structure, for example, a gantry is employed which is provided with support means allowing the structure to be guided along one axis which may be accomplished, for example, by utilizing rails. Means are provided for positioning and manipulating two sensors, for example, a bridge may be employed to so manipulate the sensors. The positioning and manipulating means are supplied with carrying means, for example, a carriage on a second axis which is perpendicular to said first axis. Tracking means are provided, for example, a rotatable carriage which allows the machine to track around a contour surface, maintaining the sensors perpendicular to the surface which carries the manipulators. Positioning means are provided which are carried by the tracking means, positioning the sensors perpendicular to the contoured surface to be investigated and maintained at a predetermined distance and speed therefrom. Means for moving the positioning means along an axis perpendicular to the first axis and the second axis are further provided. Means for sensing carried by the positioning means are provided for measuring the distances between the sensing means and the contoured surface. Additional sensing means for measuring the distance between the sensing means and the contoured surface along the compounded contour may be provided.

BRIEF DESCRIPTION OF THE PREFERRED EMBODIMENT

Figure 1:
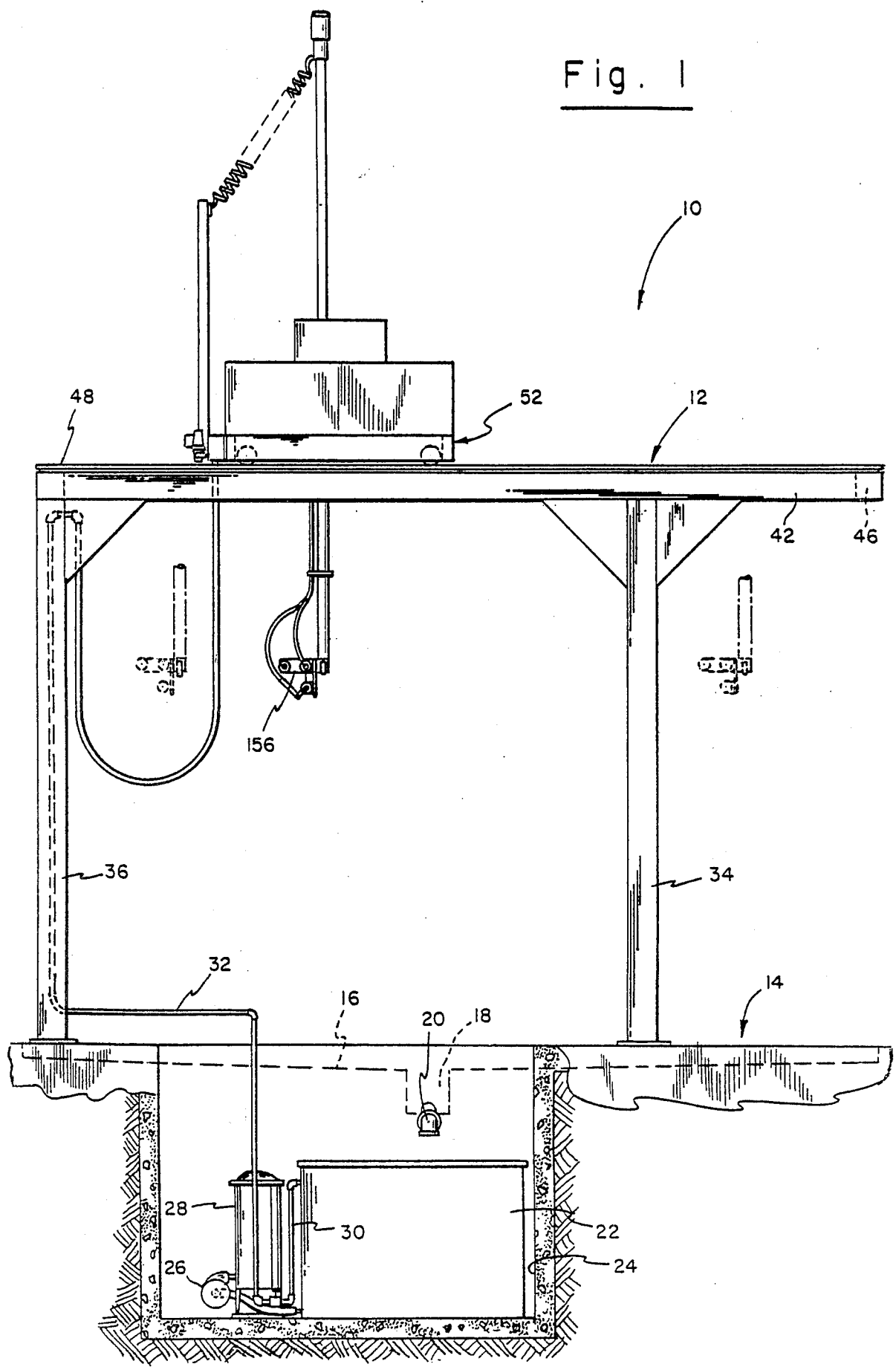
FIG. 1 is a side-elevational view of the ultrasonically controlled contour following and testing machine of this invention.
Figure 2:
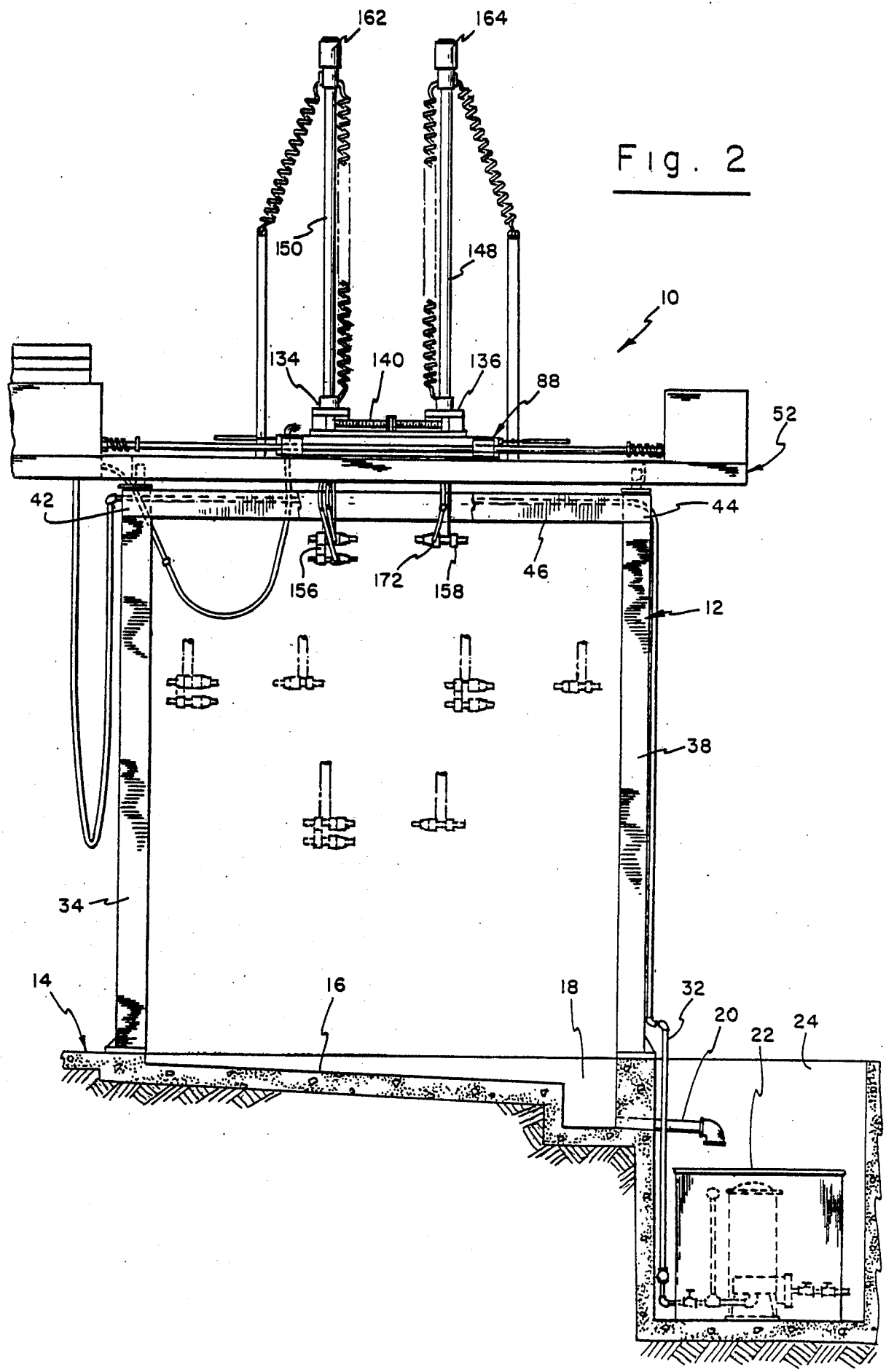
FIG. 2 is an end-elevational view thereof, as seen from the righthand end of FIG. 1.
Figure 3:
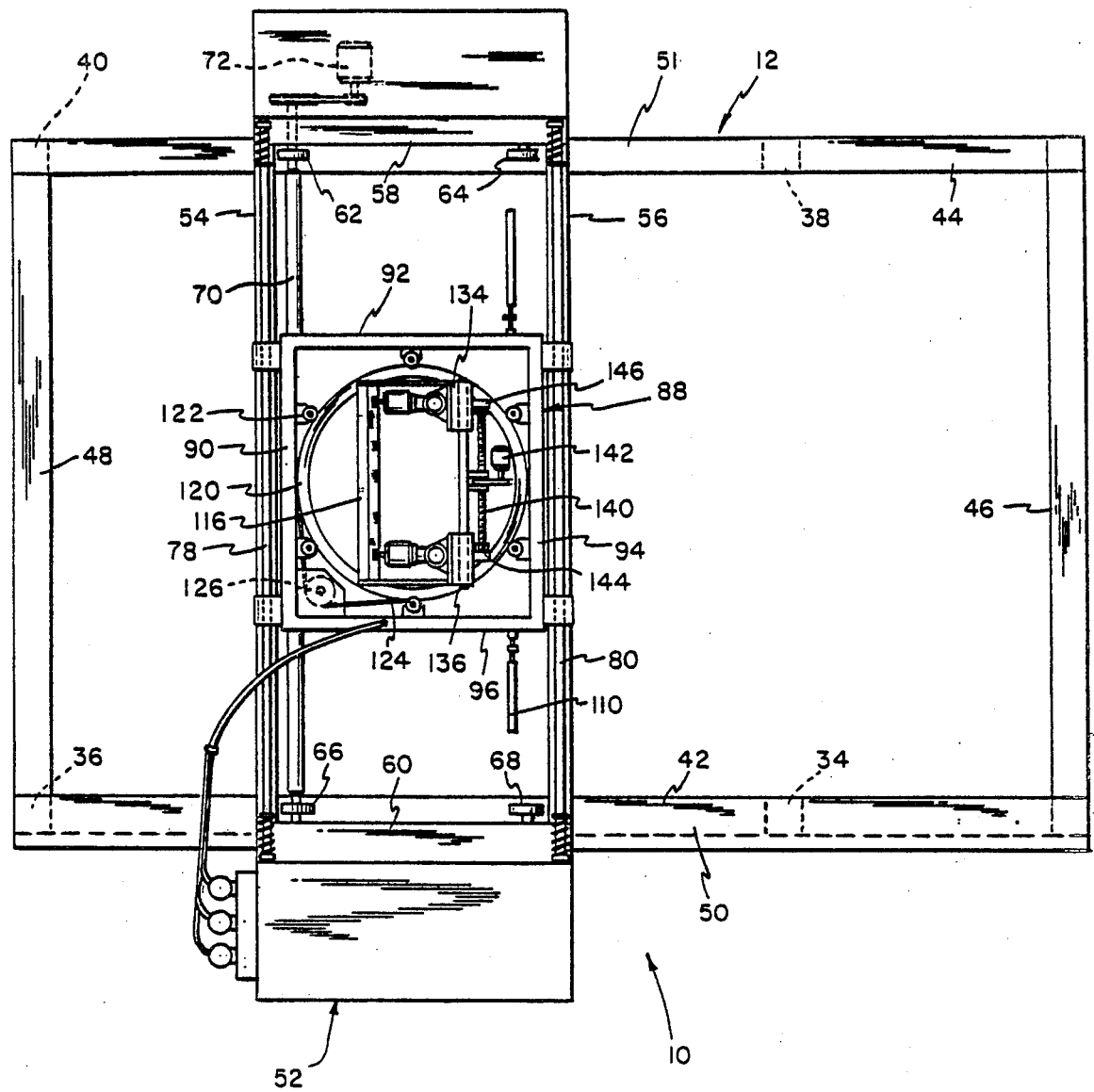
FIG. 3 is a plan view on reduced scale of the contour following and testing machine shown in FIGS. 1 and 2.

The ultrasonically controlled contour following and testing machine is generally indicated at 10 of FIGS. 1, 2 and 3. The portion of the machine 10 which is fixed on a base is the gantry 12. In view of the fact that liquid is used to couple the ultrasonic search units to the part being tested, the foundation base 14 (see FIGS. 1 and 2) has a sloping floor 16 for water drainage under the gantry 12. Water falling onto sloping floor 16 runs into sump 18, which is drained by a drain pipe 20 into open topped tank 22 positioned in pit 24 below the level of drain pipe 20.

Referring to FIG. 1, liquid is drawn from the bottom of tank 22 by pump 26. Pump 26 discharges through filter 28, which delivers filtered liquid to both recirculating line 30, which returns liquid to tank 22 and to delivery line 32. The destination of delivery line 32 will be described hereinafter.

Figure 4:
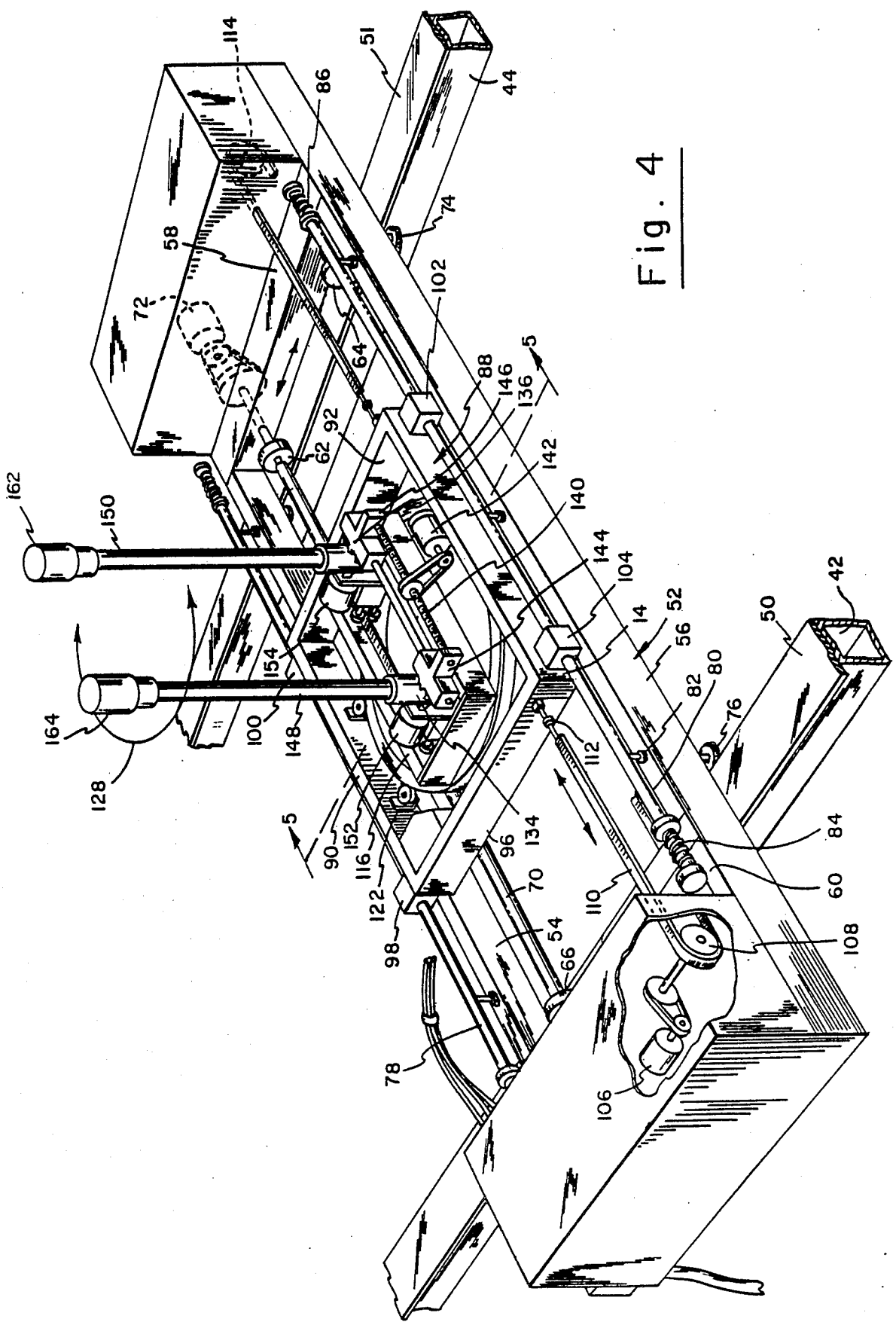
FIG. 4 is an enlarged isometric view of the bridge of the testing machine, with parts broken away and parts taken in section.

Gantry 12 is the fixed portion of testing machine 10. It comprises support columns 34, 36, 38, and 40 which are mounted on pads on foundation base 14 to provide a rigid, fixed support for the balance of the machine. Rails 42 and 44 are secured across the tops of support columns 34 and 36 and 38 and 40 respectively. Fillet plates add structural rigidity. Cross members 46 and 48 provide interconnections which enhance the rigidity of the gantry structure. The tops of rails 42 and 44 are support tracks that are flat and parallel to provide a planar running surface 50 on the top of the gantry 12. Such supplemental tracks 50 and 51 are shown in FIG. 4. As indicated in FIGS. 1, 2 and 3, gantry 12 is preferably made of square tubing of appropriate section welded together with appropriate strengtheners, fillets and diagonal braces. The length of the gantry 12 is the direction along the rails 42 and 44 and, in that direction, the space under the gantry 12 is unobstructed. (See FIG. 2.) The lengthwise direction of rails 42 and 44, left and right in FIGS. 1 and 2, define the first direction of motions of the testing machine. Curtains may be hung under the periphery of the gantry 12 to control water spray.

Bridge 52 is mounted on tracks 50 and 51 for motion thereon along the longitudinal or first direction. Bridge 52 extends across the gantry 12, see FIG. 2, at least across the top of the rails. Bridge 52 has a main frame made up of side members 54 and 56 and cross pieces 58 and 60. The side members and cross pieces are welded together into a rigid frame. Bridge 52 is supported on rotatable support wheels 62, 64, 66 and 68 so that the bridge is movable longitudinally along the gantry 12. As set forth in FIGS. 3 and 4, support wheels 62 and 66 are connected by shaft 70, which in turn is driven by motor 72 acting through a speed reducer. If desired, a position transducer can be employed to provide readout of the bridge position on its longitudinal motion across the gantry 12. If flat rails are provided, as indicated in the drawings, then guide rollers (such as guide rollers 74 and 76 and similar guide rollers under the other side of the bridge) may be employed to maintain the rectangular position of the bridge on the gantry 12. Longitudinal positioning of the bridge on the gantry 12 is detected by means of an encoder mounted on the bridge and geared to a rack secured to the gantry 12. Accordingly, pulses are produced for keeping track of bridge position.

Figure 5:
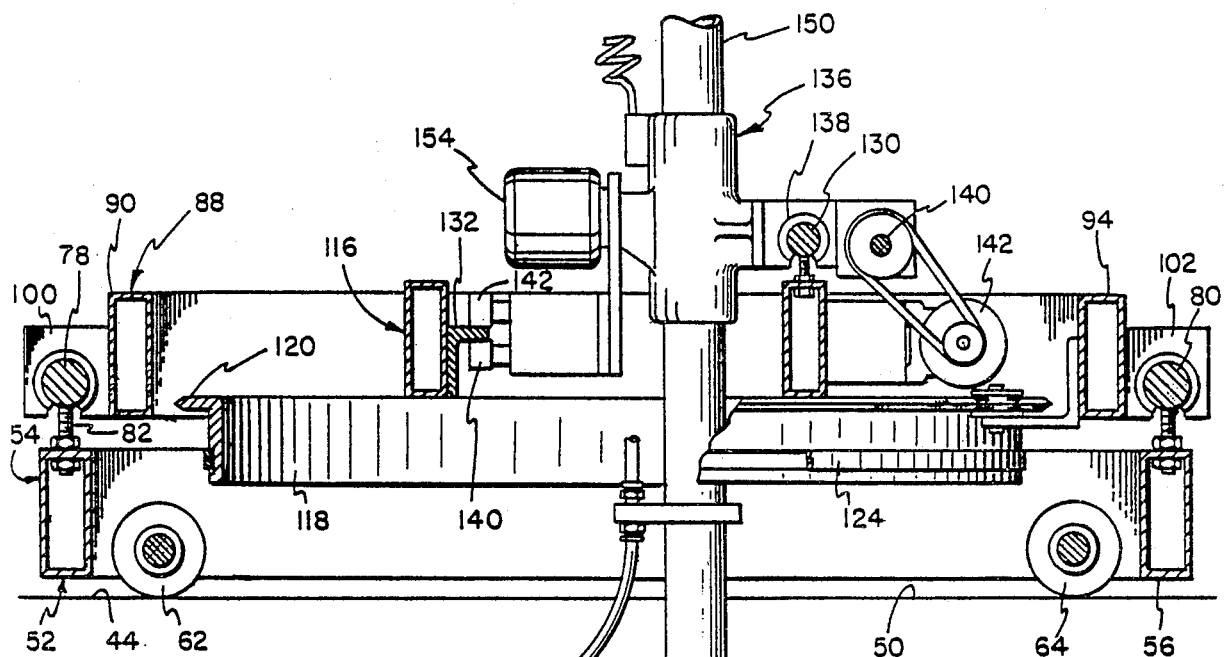
FIG. 5 is an enlarged section taken generally along the line 5—5 of FIG. 4, with parts broken away and parts taken in section.

Cylindrical carriage rails 78 and 80 are mounted on the side members 54 and 56 of the bridge. Each is mounted on a plurality of adjustable posts 82, see FIGS. 4 and 5, which are adjustably mounted with respect to the cross rails. In FIG. 5, the posts are threaded into a nut secured within the tube, and they are locked with a lock nut on the top of the side member tube. In this way, the two carriage rails 78 and 80 can be accurately aligned so that they are straight and parallel to each other. These rails define the transverse or second direction. Springs 84 and 86 are mounted on the ends of carriage rail 80 to serve as a bumper at each end thereof. Similar springs are mounted on the carriage rail 78 for the same purpose.

Carriage 88, see FIGS. 3, 4, and 5, is approximately square in its exterior configuration. It is formed of members 90, 92, 94 and 96 which are preferably tubes which are welded together in the square configuration. In order to accurately guide carriage 88 in the transverse direction and maintain low friction, ball bushings are used to support the carriage on the carriage rails. Ball bushings 98, 100, 102 and 104 are provided for this purpose. It is the ball bushings that engage upon limit springs 84 and 86 at the ends of carriage traverse to limit carriage motion.

Carriage travel in the transverse direction along its carriage rails is provided by a belt drive. As seen in FIG. 4, transverse drive motor 106 on back end of bridge is mounted on the bridge 54 and through a speed reduction drives belt pulley 108. Belt 110 is attached to carriage 88 with at least one end being tension adjustable by means of turn buckle 112. Belt 110 passes around drive pulley 114 so that its other end is also attached to carriage 88. Thus, by actuation of motor 106, carriage 88 is moved in the transverse direction across the bridge 52. Position detection can be achieved at pulley 108 providing the pulley in a non-slip relationship with the belt 110, such as by use of a toothed belt.

Rotatable carriage 116 is mounted on ring 118 which has an outwardly extending circular flange 120, see FIG. 5. Flange 120 is carried in a series of V-grooved guide rollers 122 which are mounted in carriage 88. There is a sufficient number of the V-grooved rollers 122 to provide adequate rotational support for the rotatable carriage 116. As seen in FIG. 3, six such V-grooved guide rollers are positioned around the interior of the carriage. By this means, the rotatable carriage 116 is rotatably mounted in the carriage 88. Belt 124, see FIGS. 3 and 5, encircles ring 118. Belt 124 is driven by turntable motor 126 so that rotatable carriage 116 can be rotated to any desired angular position about the vertical turntable axis, as indicated by arrows 128 in FIG. 4. The belt is toothed and controls the rotation of a sensor which indicates the angular position of the turntable.

As seen in FIGS. 3, 4 and 5, the main structure of rotatable carriage 116 is a rectangular frame made of square tubing, which, in turn, is mounted on ring 118. Guide bar 130 is mounted above one of the frame members of rotatable carriage 116, while guide rail 132 is mounted on the opposing parallel frame member.

Manipulators 134 and 136 are mounted to move along the guide bar 130 and guide rail 132. The manipulators are almost identical, and manipulator 136 is best seen in FIG. 5. Ball bushing 138 engages guide bar 130, while guide rollers 140 and 142, which are mounted on the back of the manipulator structure, engage above and below guide rail 132. By this structure, the manipulators can move toward and away from each other along the guide rail and guide bar. The distance between the manipulators is controlled by screw 140, which is rotated by spacing control motor 142. The opposite ends of screw 140 are threaded in opposite hand and respectively engage in nuts 144 and 146 mounted on manipulators 134 and 136. In this way, the manipulators are moved toward and away from each other. They are preferably equidistant from the upright turntable axis. Knowledge of the closeness of the positioning of the two manipulators is not necessary for control of the device, but such information may provide useful information with respect to the testing of the particular test structure. Thus, a position readout may be provided.

Manipulator posts 148 and 150 are vertically movably mounted within the upright oriented guide sleeves in the bodies of manipulators 134 and 136, respectively. Manipulator post motors 152 and 154 are respectively connected to move the manipulator posts 148 and 150 vertically through their guides. It is necessary to the function of the test machine that the manipulator posts be at the same height level or at a correlated height level so that a readout is provided to relate the positions of the manipulator posts with respect to each other and to energize the motors appropriately to locate them in appropriate facing positions. It is seen from the drawings that the manipulator posts move in a direction parallel to the upright axis of rotation of the turntable. The structure thus far described has sufficient flexibility and adjustability to achieve inspection of surfaces which do not have substantial curvature about a horizontal axis in addition to the expected curvature about a vertical axis. In order to permit sufficient flexibility for the testing of more complex structures, such as dish-shaped radar antennas, one further adjustable angle of orientation is necessary.

Carrier 156 is mounted on the bottom of manipulator post 150 for rotation about a horizontal axis. Carrier 158, see FIG. 2 is similarly mounted on the bottom of manipulator post 148 for rotation upon an axis parallel to the axis of rotation of carrier 156. Rotation on these axes is achieved by a worm wheel mounted on each carrier at the bottom of the post. In FIG. 5, worm wheel 160 is secured to carrier 156. At the top of manipulator post 150, carrier rotation drive motor 162 drives a worm rotating on an axis extended down through manipulator post 150 with the worm in engagement with worm wheel 162. Thus, by rotation of carrier rotation drive motor 162, carrier 156 rotates about a horizontal axis. The axis is normal to the axis passing through the two manipulator posts. A similar carrier rotation drive motor 164 mounted on top of manipulator post 148 rotates carrier 158 about its horizontal axis. In view of the fact that it is desired that the carriers be oriented at the same angle with respect to their manipulator posts, angular position information with respect to the angle of the carriers with respect to their manipulator posts is sensed and fed back to the main controller.

Figure 6:
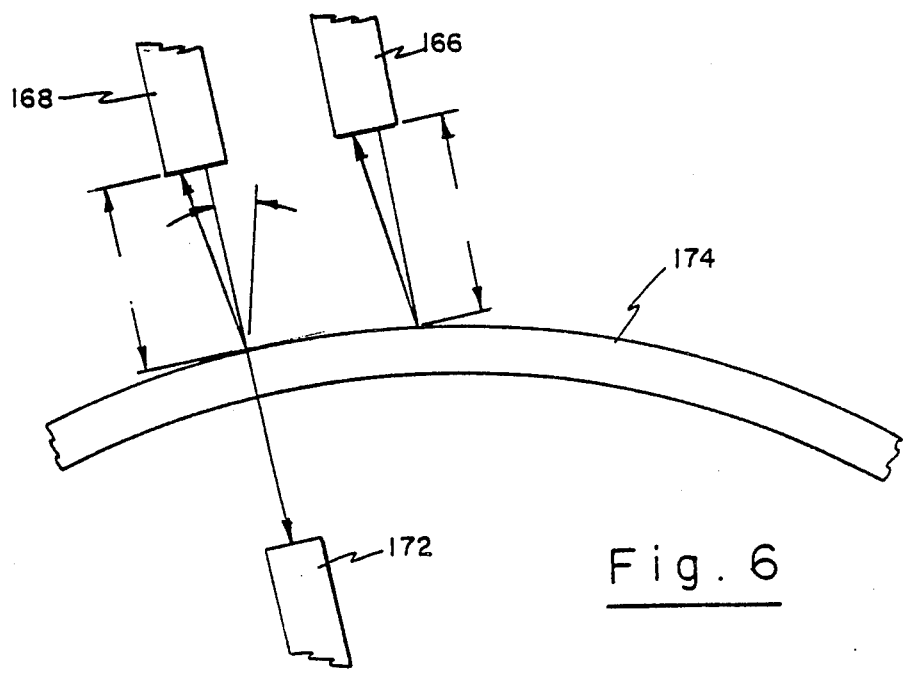
FIG. 6 is a section taken generally along a horizontal plane through a contoured structure being tested and at the level of the ultrasonic search units.

Ultrasonic units 166, 168 and 170 are mounted on carrier 156 and ultrasonic unit 172, see FIG. 2, is mounted on carrier 158. Ultrasonic units 166, 168 and 170 are combined ultrasonic transmitters and receivers. They sense the differential distance to the workpiece, such as the workpiece 174 shown in FIG. 6. Such electrical circuitry for performing this function is well known to those skilled in the art and reference is made to U.S. Pat. No. 2,743,429 to Erdman. When there is a difference indicated by units 166 and 168, the control unit to which the ultrasonic units are connected causes rotation of rotatable carriage 116 so that the distance is equalized. In those cases where there is substantial curvature in the vertical direction, that is changes in surface angle up and down the workpiece, then the differential distance measured by ultrasonic units 166 and 170 causes the controller to energize the carrier rotation drive motors to rotate the carriers so that ultrasonic units 166 and 170 are equidistant from the surface of the workpiece. Each of the ultrasonic units is provided with a water jet to provide the liquid column coupling between the ultrasonic unit and the workpiece. The three ultrasonic units 166, 168 and 170 on carrier 156 each operate as a reflective distance sensor for the purpose of making the above described adjustments. In addition, the absolute distance from the face of ultrasonic unit 168 is controlled to be half the distance between the ultrasonic units 168 and 172. The spacing of the ultrasonic unit 168 from the workpiece is controlled by bridge and carriage motion. The distance between ultrasonic units 168 and 172 is preset by the spacing between manipulators 134 and 136 in accordance with the thickness of the workpiece. Ultrasonic unit 172 is a signal receiving sensor only and receives the portion of the ultrasonic signal emitted from ultrasonic unit 168 and transmitted through the workpiece 174. Thus, the test machine works on the basis of ultrasonically testing by through transmission of the ultrasonic waves.

In a particular test setup, a workpiece to be tested is positioned with its curvature in an upright direction, with the axis of curvature generally parallel to the upright turntable axis. The longer dimension of the workpiece is positioned generally parallel to the rails 42 and 44. The height of the sensors is initially set by an initial position of the manipulator post 148 and 150. The space between the posts is established by the thickness of the workpiece so that the proper clearance exists between the faces of the ultrasonic unit and the workpiece. The test machine is then controlled to make a first pass. The test machine is set to provide a constant surface speed of testing. As the rotatable carriage 116 is rotated, the angle of the rotary carriage provides both the sine and cosine of its angle for determining the respective orthogonal speed requirements on the transverse and the longitudinal paths. For example, a 30 degree turntable angle prescribes a 50 percent speed on the transverse path of the carriage across the bridge and an 87 percent speed of the bridge along the gantry 12. The sine-cosine speed values proportion the basic orthogonal axis scan speeds. A constant surface scan speed is thereby maintained, regardless of the turntable angle. At the end of a pass, the manipulator posts are lowered one test increment, and the scan is made in the opposite direction. This scanning is repeated until testing is complete. The testing machine thus allows precise positioning of the ultrasonic units over smooth horizontal curved surfaces, such as air-foil shape and is not restricted to positioning over shapes defined by mathematical expression. While the testing machine described is useful as a through transmission ultrasonic inspection method incorporating a water column for ultrasonic coupling and is particularly suited for bonded panels, it is also possible to employ pulse/echo type ultrasonic sensing units for the testing and inspection function. With the employment of an ultrasonic unit 172 which independently measures the energy transmitted through the workpiece, then the two manipulators can be separated in accordance with workpiece thickness so that each of the ultrasonic units is properly spaced from the workpiece independent of workpiece thickness. In this way, the test machine can be used for structures of varying thickness.

This invention having been described in its preferred embodiment, it is clear that it is susceptible to numerous modifications and embodiments within the ability of those skilled in the art and without the exercise of the inventive faculty. Accordingly, the scope of this invention is defined by the scope of the following claims.

Therefore, what is claimed is:

1. A contour following and testing machine comprising:
  a gantry, at least one rail on said gantry, said rail defining a longitudinal direction;
  a bridge, bearing means on said bridge for engaging one said rail on said gantry so that said bridge is movable on said gantry in said longitudinal direction, a carriage rail on said bridge, said carriage rail being oriented at an angle to the longitudinal direction to define a transverse direction;
  a first carriage, said first carriage being movably mounted on said carriage rail on said bridge so that said carriage can move in the transverse direction;
  a rotatable carriage, said rotatable carriage being rotatably mounted on said first carriage for rotation about an axis which is at an angle with respect to both the longitudinal and transverse directions;
  a manipulator mounted on said rotatable carriage, said manipulator including a bearing sleeve;
  a manipulator post mounted in said bearing sleeve for movement in a direction generally parallel to the axis of said rotatable carriage; and
  first and second sensors mounted on said manipulator post, said first and second sensors being connected so that sensing of the differential distance between the sensors and a structure to be tested is connected to rotate said rotatable carriage on said first carriage to maintain a substantially zero differential distance between said sensors and the structure being tested.

2. The contour following and testing machine of claim 1 wherein said gantry has first and second rails, said first and second rails being substantially parallel to each other, means attached to said first and second rails for fixing said rails with respect to a support so that said first and second rails form a fixed reference to the moving portions of said contour following machine.

3. The contour following and testing machine of claim 2 wherein said support means comprises support columns for supporting said first and second rails above the base from which it is supported.

4. The contour following and testing machine of claim 3 wherein the base on which said contour following and testing machine is supported includes a sloping floor and a sump below said sloping floor, a tank in said sump and a circulating pump attached to said tank so that liquid draining beneath said gantry runs to said tank and said pump recirculates the liquid.

5. The contour following and testing machine of claim 3 wherein cross members are connected between said gantry rails adjacent the ends of said gantry rails to fix the spacing between said gantry rails to that the bridge may run therealong in the longitudinal direction without crossing said cross members.

6. The contour following and testing machine of claim 2 wherein a motor is mounted on said bridge and a drive wheel on said bridge engages said gantry, said motor being connected to said drive wheel to drive said bridge along said gantry.

7. A contour following machine comprising:
  a gantry having a rail thereon, said rail being oriented in a longitudinal direction;
  a bridge movably mounted on said gantry for movement in the longitudinal direction, a motor interengaged between said gantry and said bridge for moving said bridge in the longitudinal direction, at least one carriage rail on said bridge, said carriage rail being oriented in a transverse direction at an angle to the longitudinal direction;
  a first carriage mounted on said carriage rail for movement therealong in the transverse direction, a motor interconnected between said bridge and said carriage for moving the carriage in the transverse direction, said carriage rail being a cylindrical rail and said first carriage carrying thereon ball bushings engaging said cylindrical carriage rail for guidance of said carriage in the transverse direction;
  a rotatable carriage support means on said first carriage for rotatably supporting said rotatable carriage for rotation in a horizontal plane;
  at least one manipulator on said rotatable carriage, said manipulator including a bearing sleeve, a manipulator post extending through said bearing sleeve for motion along the length of the manipulator post, said manipulator post being substantially parallel to the axis of rotation of said turntable; and
  at least two proximity sensors mounted on said manipulator posts, said proximity sensors being spaced in a direction transverse to said rotatable carriage axis so that rotation of said rotatable carriage on its axis can move said sensors to equidistant position from a surface being sensed.

8. The contour following machine of claim 7 wherein a position sensor is connected to said first carriage to sense the position of said first carriage with respect to said bridge.

9. The contour following machine of claim 7 wherein a stop limits the transverse motion of said first carriage on said bridge.

10. The contour following machine of claim 7 wherein there are two parallel cylindrical carriage rails on said bridge and said first carriage has thereon two ball bushings, one engaging each of said carriage rails for guiding said carriage in a transverse direction.

11. The contour following machine of claim 10 wherein said first carriage has a generally open center and has guide rollers thereon directed toward the open center, said rotatable carriage being positioned within the open center of said first carriage and engaging on and being supported by said guide rollers.

12. The contour following machine of claim 11 wherein a rotatable carriage drive motor is mounted on said first carriage and engages said rotatable carriage for rotating said rotatable carriage with respect to said carriage.

13. The contour following machine of claim 12 wherein an angular position detector is mounted on said first carriage and is connected to said rotatable carriage for measuring and indicating the angular position of said rotatable carriage with respect to said first carriage.

14. The contour following machine of claim 13 wherein there are two manipulators on said rotatable carriage, said manipulators being positioned on opposite sides of the axis of said rotatable carriage, said two manipulators each carrying a manipulator post, both of said posts being oriented substantially parallel to the axis of said rotatable carriage, one of said posts carrying said proximity sensors and said proximity sensors being ultrasonic proximity sensors, and the other of said manipulator posts carrying an ultrasonic sensor.

15. An ultrasonically controlled contour following and testing machine comprising:
a gantry defining a longitudinal direction;
a bridge movably mounted on said gantry for moving in the longitudinal direction and for defining a transverse direction;
a first carriage mounted on said bridge for movement on said bridge in the transverse direction and for rotatably carrying a rotatable carriage thereon;
a rotatable carriage rotatably mounted on said first carriage for rotation on an axis at an angle to both said longitudinal and transverse direction, said rotatable carriage having first and second manipulators thereon, first and second manipulators, said manipulator posts being movable in a direction generally parallel to said rotatable carriage axis;
ultrasonic sensors mounted on said manipulator posts so that said manipulator posts can be positioned on opposite sides of a structure to be tested so that said ultrasonic sensors are positioned on opposite sides of the structure to be tested, said manipulator posts being driven so that said sensors on said manipulator posts are in alignment with each other on opposite sides of the structure to be tested.

16. The ultrasonically controlled contour following and testing machine of claim 15 wherein a guide bar is positioned across said rotatable carriage and both of said manipulators are movably mounted with respect to said guide bar so that the distance between said manipulators can be controlled.

17. The ultrasonically controlled contour following and testing machine of claim 16 wherein a drive motor is mounted on said rotatable carriage, said drive motor being connected to both of said manipulators to move both of said manipulators toward and away from the axis of said rotatable carriage.

18. The ultrasonically controlled contour following and testing machine of claim 17 wherein said guide bar is a cylindrical rod and a ball bushing on each of said manipulators engages said guide bar so that both of said manipulators are guided along the same guide bar.

19. The ultrasonically controlled contour following and testing machine of claim 17 wherein said motor drives a screw and each of said manipulators carries a nut in screwthread engagement with said screw so that rotation of said motor moves said manipulators with respect to the axis of said turntable.

20. The ultrasonically controlled contour following and testing machine of claim 19 wherein a guide rail is also positioned on said rotatable carriage and each of said manipulators also is movably mounted with respect to said guide rail.

21. The ultrasonically controlled contour following and testing machine of claim 16 wherein a manipulator post motor is mounted on each of said manipulators, said manipulator post motors each moving said manipulator post with respect to said manipulators to control the distance said manipulator post extends from said manipulators.

22. The ultrasonically controlled contour following and testing machine of claim 21 wherein first and second carriers are respectively mounted on said first and second manipulator posts, said first and second carriers each carrying ultrasonic search units thereon, said carriers being rotatably mounted on a generally horizontal axis so that said search units can be rotated in a substantially upright plane.

23. The ultrasonically controlled contour following and testing machine of claim 22 wherein a motor is connected to each of said carriers for rotating said carriers with respect to said manipulator posts.

24. An ultrasonically controlled contour following and testing machine comprising:
a gantry;
a bridge movably mounted on said gantry for movement in the longitudinal direction;
a first carriage movably mounted on said bridge for movement in the transverse direction at an angle to the longitudinal direction;
a rotatable carriage rotatably mounted on said first carriage for rotation on an axis at an angle to the longitudinal and transverse directions of motion;
manipulators mounted on rotatable carriage on opposite sides of the axis of turntable rotation, said rotatable carriage carrying a guide rail thereon, said manipulators being movably mounted for movement along said guide bar, a motor connected to both of said manipulators for moving both of said manipulators toward and away from each other on opposite sides of the axis of rotatable carriage; and
a manipulator post movably mounted in each of said manipulators, each said manipulator post carrying thereon ultrasonic testing units for ultrasonic testing of a structure positioned between said manipulator posts and between said ultrasonic test units.

25. The ultrasonically controlled contour following and testing machine of claim 24 wherein a carrier is pivotably mounted adjacent an end of each of said manipulator posts, said carriers being mounted for rotation with respect to said manipulator posts on axes parallel to each other and at an angle to the axis of rotation of said rotatable carriage, said carriers being rotatable and said manipulator post being extendable through said manipulator so that said ultrasonic units remain in alignment.

26. The ultrasonically controlled contour following and testing machine of claim 25 wherein two proximity sensing ultrasonic testers are mounted on one of said carriers spaced circumferentially about the axis of rotation of said rotatable carriage and control means interconnects said sensors and means to rotate said turntable for maintaining the proximity sensors substantially equidistant from the structure to be tested.

27. A contour following and testing apparatus for testing the surface of a contoured workpiece, said apparatus including:
   a support structure;
   means operable in conjunction with said support structure for supporting said support structure and for guiding said support structure along a first axis;
   bridge means engaging said supporting and guiding means and being moveable on said support structure on a second axis, said second axis being normal to said first axis;
   sensing means;
   means for carrying said sensing means, said carrying means being rotatably mounted on said bridge means for rotation about a third axis, said third axis being normal to said first and said second axis;
   positioning means on said carrying means for positioning said sensors normal to the surface of the contoured workpiece and for maintaining a predetermined distance between said contoured surface and said sensing means; and
   means for maintaining a constant scan speed of said sensing means relative to the surface of the contoured workpiece.

28. The apparatus as defined in claim 27 wherein said sensing means includes a first sensor for testing the contoured workpiece and a second sensor for sensing the spacing difference between said first sensor and the surface of said contoured workpiece and the second sensor and the surface of said contoured workpiece, and for causing said sensors to move to a position in which said spacing difference is zero.

29. The apparatus as defined in claim 27 wherein said sensing means includes:
   a first ultrasonic sensor adapted to be ultrasonically coupled to said positioning means and stationed in test relation to the workpiece;
   a second ultrasonic sensor adapted to be ultrasonically coupled to said positioning means and positioned in parallel alignment and on the same plane with said first sensor and being stationed in test relation with said workpiece, and
   wherein said positioning means is coupled to said rotatable carrying means and is responsive to said first sensor and said second sensor for measuring the distances between said first sensor and said workpiece and said second sensor and said workpiece, and rotates said rotatable carrying means until the distances between said first sensor and said workpiece and said second sensor and said workpiece are equal.

30. The apparatus as defined in claim 29 wherein said sensing means further includes a third sensor stationed in test relationship with said workpiece on the side opposite said first and second sensors and in substantial alignment with said first sensor for through transmission testing, said third sensor being coupled to said positioning means for rotation with said carrying means so as to be maintained normal to said workpiece and in alignment with said first sensor.

31. The apparatus as defined in claim 30 wherein said first, second and third sensors are ultrasonic search units.

32. A contour following and testing apparatus comprising:
   at least one test sensor;
   means for supporting and guiding said at least one test sensor along first, second and third mutually perpendicular axes, around said third axis and around a fourth axis parallel to said first and second axes;
   at least one position sensor mechanically connected to said test sensor; and
   means operative to receive position signals from said at least one position sensor, and to control said supporting and guiding means so as to maintain said at least one test sensor perpendicular to the contoured surface of a testpiece and to maintain a constant scan speed of said at least one test sensor relative to the contoured surface of the testpiece.

* * * * *